(12) United States Patent
Malandruccolo, Jr.

(10) Patent No.: US 8,273,064 B2
(45) Date of Patent: Sep. 25, 2012

(54) APPARATUS FOR SANITIZING BENEATH A WORN MEDICAL CAST

(75) Inventor: John A. Malandruccolo, Jr., Auburn, NY (US)

(73) Assignee: MD Americas, LLC, Auburn, NY (US)

( * ) Notice: Subject to any disclaimer, the term of this patent is extended or adjusted under 35 U.S.C. 154(b) by 263 days.

(21) Appl. No.: 12/727,835

(22) Filed: Mar. 19, 2010

(65) Prior Publication Data

US 2011/0230847 A1 Sep. 22, 2011

(51) Int. Cl.
*A61F 13/00* (2006.01)
*A61F 5/00* (2006.01)

(52) U.S. Cl. ............... 604/304; 604/308; 602/8; 602/21

(58) Field of Classification Search .................. 604/290; 601/37; 602/8, 21
See application file for complete search history.

(56) References Cited

U.S. PATENT DOCUMENTS

| | | |
|---|---|---|
| 2,711,731 A | 6/1955 | Krohne |
| 3,527,208 A | 9/1970 | Hoegerman |
| 4,475,836 A | 10/1984 | Colognori |
| 4,667,659 A | 5/1987 | Hayday |
| 4,892,091 A | 1/1990 | Sullenger |
| 4,945,903 A * | 8/1990 | Alper .................. 602/5 |
| D342,999 S | 1/1994 | Gonsalves, Jr. |
| D370,729 S | 6/1996 | Hurlburt et al. |
| D372,978 S | 8/1996 | Harvey |
| D417,281 S | 11/1999 | East |
| D443,114 S | 5/2001 | Burrell et al. |
| D479,759 S | 9/2003 | Johnson |
| D546,451 S | 7/2007 | Givens, Jr. |
| 2006/0184078 A1 | 8/2006 | Robertson et al. |

FOREIGN PATENT DOCUMENTS

JP 2000005248 A 1/2000

* cited by examiner

*Primary Examiner* — Jacqueline F. Stephens
(74) *Attorney, Agent, or Firm* — Hiscock & Barclay, LLP

(57) ABSTRACT

An apparatus for sanitizing the skin area beneath a worn medical cast includes a thin elongate and flexible member made from a highly pliable material, the member including a distal end having at least one cleaning pad secured thereon. The thin elongate member is sized to be fitted between the skin of a cast wearer and the inner surface of a worn cast. In one version, disposable cleaning pads are releasably secured to the distal end of the elongate member.

20 Claims, 2 Drawing Sheets

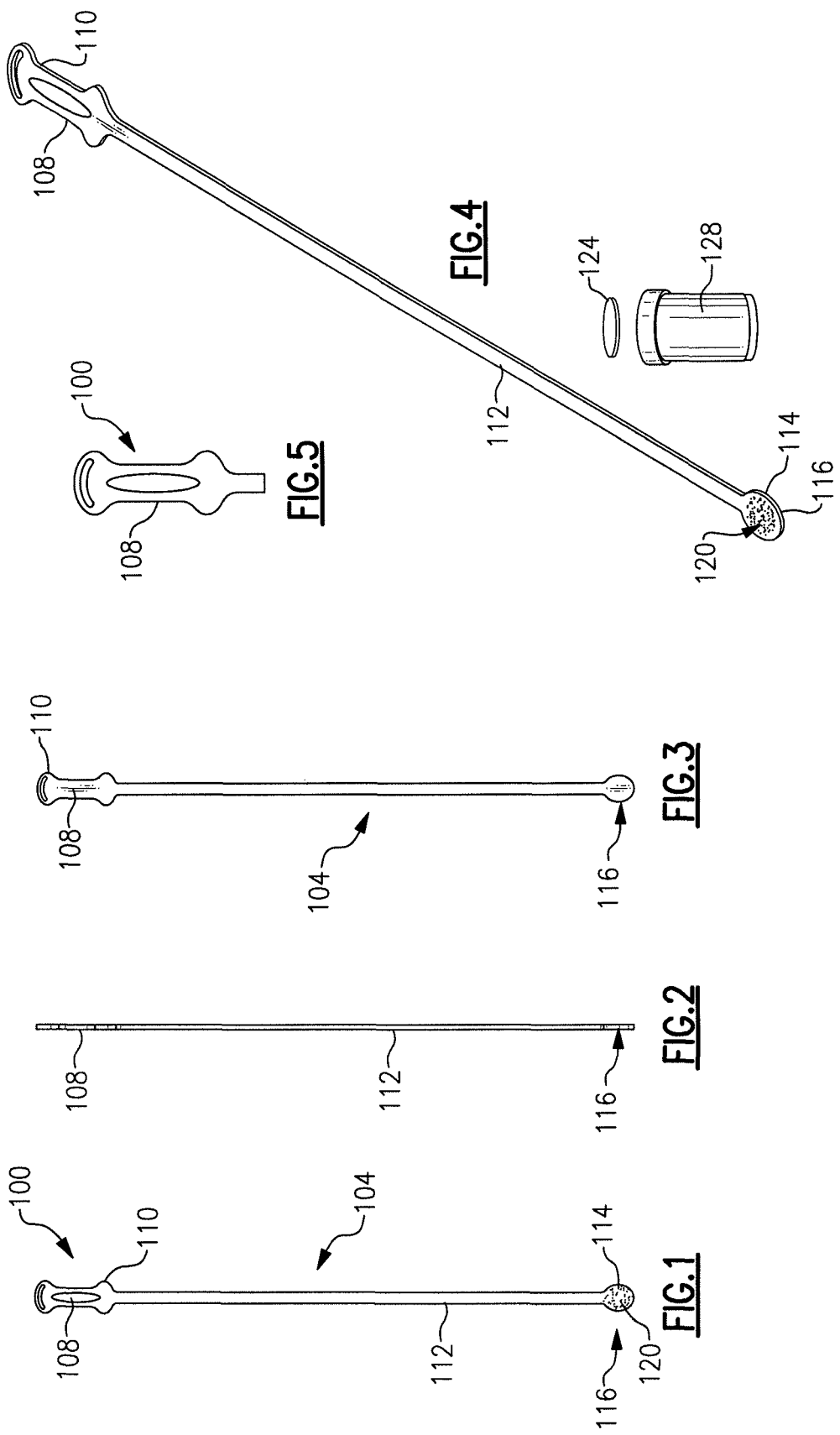

APPARATUS FOR SANITIZING BENEATH A WORN MEDICAL CAST

FIELD OF THE INVENTION

The application generally relates to the field of orthopedic apparatus and devices. More specifically, this application relates to an apparatus and related method for periodically cleaning the skin areas beneath the worn medical cast of an individual so as to allow routine maintenance of typically inaccessible skin areas.

BACKGROUND OF THE INVENTION

It is well known that incidents or accidents can routinely occur, producing broken bones and/or creating other forms of injuries to individuals that require a hard or soft medical cast to be worn on a limb (i.e., an arm or leg) or other extensive body area of a patient for an extended period of time. This period of time can easily extend over several months, usually depending on the extent of the injury. A typical cast can cover a substantial portion or even the entirety of a patient's limb (i.e., leg, arm). As a result, the ability of the cast wearer to maintain daily personal hygiene by means of washing, bathing, showering and the like is severely compromised in that the skin area that is covered by the worn cast is simply not accessible for routine cleaning. As a result, excess skin develops in these body areas, as well as latent accumulations of dirt, bacteria, sweat, as well as other undesirable byproducts. The passage of time simply exacerbates these conditions and increases any annoyances and discomfort that are already afforded to the cast wearer. To date, there has not been an effective means that has been provided for cleaning the skin areas, relieving the itching that develops, or otherwise tending to the latent buildup of sweat and dirt beneath the cast of the wearer.

A number of orthopedic devices, such as described, for example, in U.S. Pat. No. 2,711,731, describe an instrument designed to relieve itching as encountered by a patient wearing a hard plaster medical cast. The instrument includes a long resilient member stamped from stainless steel or similar material, the instrument having at least one end formed as a pad. The pad includes a plurality of smooth outwardly extending projections.

Another itch relieving device is generally described in U.S. Pat. Nos. 4,667,659 and 4,892,091. According to each design, a strip-like member includes a plurality of protrusions formed along the entire length or substantial length of the device. The protrusions are rounded to enable temporary relief of itching caused by cast wear. A number of other similar devices are known, also typically for reaching typically inaccessible locations, such as beneath a cast or behind a user's back, for the relief of itching. While itch relief is provided, none of the above-noted devices provide any option as to cleaning or otherwise sanitizing the skin surface beneath the worn medical cast.

As a result, there is a general need in the field of orthopedic devices and apparatus to provide a sanitizing apparatus for cast wearers.

SUMMARY OF THE INVENTION

According to one aspect, there is provided an apparatus for cleaning the skin beneath a medical cast, said apparatus comprising a thin elongate member made from a highly flexible material and at least one cleaning pad, wherein said at least one cleaning pad is disposed at one end of said flexible member, said member being sized to fit between the skin of a cast wearer and the inner surface of a cast.

According to one version, the elongate member releasably receives a cleaning pad at a distal end thereof, the member including means for attaching the cleaning pad thereto. According to one version, the cleaning pad is coated with a sanitizing or other cleansing agent, the pad being made from a material, such as cotton, wherein the elongate member is equipped with one of hook and loop fasteners that enables releasable adhesion. The pads preferably can be disposable. According to another version, the cleaning pad includes an adhesive or other suitable backing. A supply of cleaning pads, preferably those that have been prepared with a cleaning or disinfecting solution, can be used in connection with the elongate member.

According to another version, the elongate member and the at least one cleaning pad can be integrated, wherein the apparatus is disposable or intended for "single patient" use.

According to another aspect of the invention, there is provided an apparatus for cleaning the skin of a cast wearer, said apparatus comprising a thin, flexible and elongate member having a distal end and an opposing proximal end, said flexible and elongate member having a thickness that permits said member to be slidingly movable between the skin area of a patient and the inner surface of a worn cast; and a cleaning pad disposed on said distal end, said distal end including means for releasably attaching said cleaning pad, said cleaning pad having a skin cleansing agent disposed thereon.

According to yet another aspect, there is provided a method for cleaning the skin area beneath the worn medical cast of a patient, said method comprising the steps of:

securing a cleaning pad to the distal end of a thin elongate plastic member, said member having a thickness dimension which permits the member to be inserted between the cast and the skin of the patient and a length dimension that permits the distal end of said member to be situated anywhere beneath the worn cast; and moving said flexible member so as to move said cleaning pad within the cast to clean the area of skin covered by the worn medical cast.

One advantage of the present invention is that routine care and maintenance of a patient are made possible, without difficulty in that the herein described sanitizing apparatus is easily manipulated through one handed operation. As such, the apparatus can be easily handled and used effectively by the patient.

Another advantage is that the herein described sanitizing apparatus is relatively simple to manufacture and produce, while being highly effective.

Yet another advantage is that the herein described apparatus is made with smooth rounded edges, thereby avoiding scraping, cutting or otherwise aggravating the sensitive skin area beneath the worn cast.

In one version, the distal end of the herein described apparatus can include a recessed attachment surface in order to reduce the chance of adherence of the hook fasteners with the inner padding material of a worn cast.

These and other features and advantages will be readily apparent from the following Detailed Description, which should be read in conjunction with the accompanying drawings.

BRIEF DESCRIPTION OF THE DRAWINGS

FIG. 1 is a top plan view of an under cast sanitizing apparatus, which is made in accordance with one embodiment of the present invention;

FIG. 2 is a side elevational view of the under cast sanitizing apparatus of FIG. 1;

FIG. 3 is a bottom plan view of the under cast sanitizing apparatus of FIGS. 1 and 2;

FIG. 4 is a top perspective view of the under cast sanitizing apparatus of FIGS. 1-3 including a supply of cleaning pads;

FIG. 5 is an enlarged view of the handle portion of the under cast sanitizing apparatus of FIGS. 1-4;

DETAILED DESCRIPTION

Figure 6:
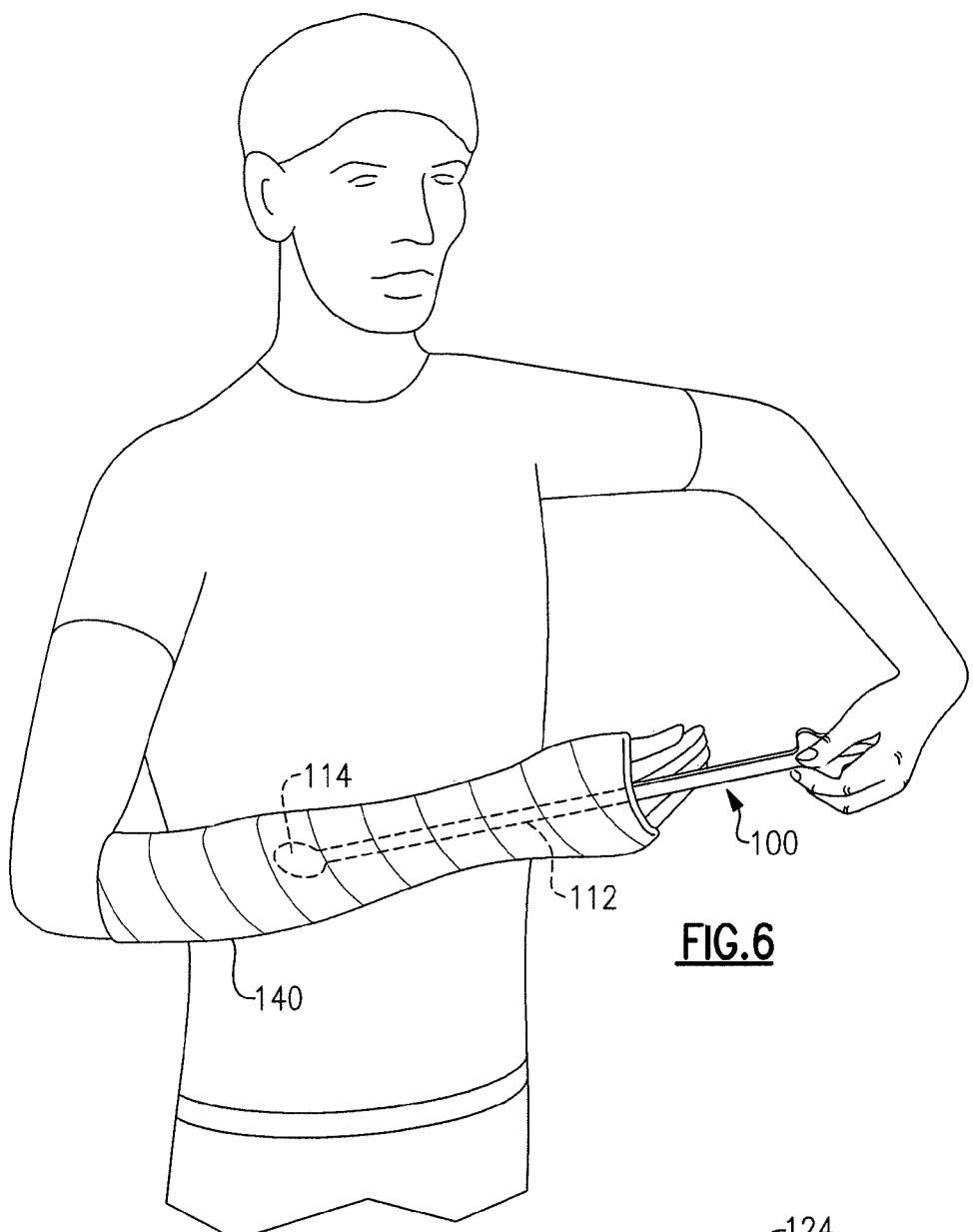
FIG. 6 is a perspective view of the under cast cleaning apparatus of FIGS. 1-4, in a use condition.

The following description relates to a preferred embodiment of an under cast sanitizing apparatus in accordance with the present invention. Throughout the course of discussion, several terms are used in order to provide a suitable frame of reference with regard to the accompanying drawings, such as "distal", "proximal", "top", "bottom", "above", "below" "upper", "lower" and the like. It is not intended that these terms be overly limiting with regard to the claims that follow, except where so specifically indicated.

Referring to FIG. 1, there is depicted an under cast sanitizing apparatus 100 that is made in accordance with a preferred embodiment. The under cast sanitizing apparatus 100 is defined by a thin, flexible and elongate member 104, the member being made according to this embodiment from a highly pliable plastic, such as polypropylene, For purposes of the herein described apparatus, literally any material can be substituted provided the material is biocompatible and also sufficiently flexible and pliable to permit fitting beneath the cast of a wearer such that the apparatus 100 can suitably and malleably conform, as needed, to the underlying shape and contour of the patient's limb (e.g., an arm, leg).

Referring to FIGS. 1-3, the flexible and elongate member 104 is defined by a handle portion 108 at a proximal end 110, an intermediate extending portion 112 and an adhesive pad receptacle or adhesive pod 114 formed at an opposite distal end 116. The handle portion 108 of the herein described apparatus 100 has a wider dimension, as compared with that of the intermediate extending portion 112, thereby enabling one-handed operation by a wearer for purposes of its use. The length and thickness dimensions of the intermediate extending portion 112 of the elongate member 104 are sufficient to permit the herein described apparatus 100 to be easily slid and maneuvered through the entirety of a full leg or a full arm cast between the inner surface of the as worn cast and the skin area of the wearer, although this parameter can be suitably varied for smaller sized casts, as needed. Moreover, each of the intermediate extending portion 112 and the distal end 116 are fabricated with smooth rounded edges in order to avoid abrading with the skin surface area beneath the worn cast, as described below.

According to this specific embodiment, the elongate member 104 has an overall length dimension as measured from its proximal end 110 to its distal end 116 of approximately 533 mm (approximately 21 inches), wherein the member is approximately 2.6 mm (approximately 0.10 inches) thick overall and is defined by a width dimension along the intermediate extending portion 112 of approximately 9.5 mm (approximately 0.37 inches). These parameters can be suitably varied, depending on the application provided the intermediate extending portion and the distal end, having a cleaning pad as attached thereto, as described below, can be easily and slidingly moved beneath the worn cast. The elongate member 104 can be reused or constructed as a disposable or "single patient" device that can be used during the period that a medical cast is worn.

The cleaning pad receptacle 114 is defined according to this embodiment by a planar surface on one facing side at the distal end 116 of the elongate member 104. A plurality of one of either hook or loop fasteners 120 are disposed on the planar surface of the distal end 116. According to one embodiment, the planar surface is recessed to permit attachment and prevent inadvertent attachment between the hook fasteners and the inner padded material of a worn medical cast. Each of the cleaning pads 124, FIG. 4, themselves can be made from a material, such as cotton, that has been pre-treated with a biocompatible cleaning solution. One preferred cleaning solution for purposes of an exemplary embodiment includes a mixture consisting of deionized water, denatured alcohol, glycerin, PEG shea butter, cetearyl isononanoate, ceteareth-20, cetearyl alcohol, glyceryl stearate, ceteareth-12, etylpalmitate and allotonin. Other suitable pad materials can be used such as nonwoven fabric material. According to this embodiment, the cleaning pads 124 are retained as a plurality (e.g., 12, 16, 24, etc) in a stacked arrangement within a container 128, such as a sealable jar, allowing easy removal and replacement.

Figure 7:
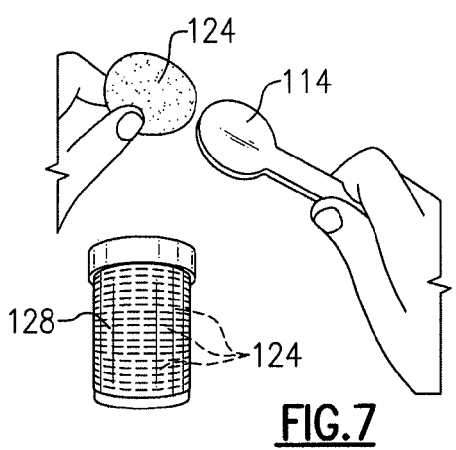
FIG. 7 is a perspective view of the cleaning pads as used in connection with the under cast sanitizing apparatus of FIGS. 1-4.

In operation and referring to FIGS. 6 and 7, the elongate member 104 and cleaning pads 124 form component parts of a kit wherein the user removes one of the medicated cleaning pads from the container 128 and attaches same to the planar surface of the cleaning pod 114, the hook fasteners providing releasable securement thereto. The user then inserts the distal end 116 of the apparatus 100 between the skin of the patient and the inner surface of the worn cast 140, FIG. 6, with the cleaning pad side of the distal end 116 facing the skin. The user than grips the handle portion 108 and slides the apparatus 100 as needed in a reciprocal fashion in and out of the worn cast 140, cleaning the limb where accessible. As previously noted, the apparatus 100 and particularly the intermediate extending portion 112 and the distal end 116 are sufficiently pliable to conform to the spacing between the skin and the inner padding area of the cast 140, wherein the rounded edges facilitates movement without skin surface abrasions. As a result, the injured limb can be periodically cleaned, reducing itch and discomfort as well as odor that also develops beneath the cast over time.

Referring to FIG. 7, the used cleaning pad 124 can be removed from the adhesive pod 114 of the elongate member 104 and discarded following use wherein the apparatus 100 can then be reused with a fresh medicated cleaning pad 124. Alternatively, the entire elongate member and pad can be made integrally, wherein each would be used as a disposable component.

PARTS LIST FOR FIGS. 1-7

100 apparatus, under cast sanitizing
104 flexible elongate member
108 handle portion
110 proximal end
112 intermediate extending portion
114 cleaning pad receptacle
116 distal end
120 hook or loop fasteners
124 cleaning pads
128 container
140 cast, medical It will be appreciated that variations and modifications are possible within the intended ambits of the herein described invention, according to the following claims.

The invention claimed is:

1. An apparatus for sanitizing the skin area beneath a medical cast worn by a person, said apparatus comprising:
    a thin flexible and elongate member made from a highly pliable material, said member being entirely separate from said cast and comprising:
        a grippable handle portion at a proximal end of said member;
        a cleaning pod formed at the distalmost end of said member opposite from said grippable handle portion; and
        an elongated intermediate section spanning said cleaning pod and said handle portion, said cleaning pod including means for receiving a cleaning pad which is secured thereto, said apparatus being further configured for gripping said handle portion with one hand by the person wearing said cast and reciprocally moving the cleaning pod and at least a portion of said intermediate section of said elongate member between the skin area of a cast wearer and the inner surface of a cast to enable periodic cleaning thereof.

2. An apparatus as recited in claim 1, wherein said cleaning pad is releasably secured to the cleaning pod of said elongate member.

3. An apparatus as recited in claim 2, wherein said cleaning pod includes at least one of hook and loop fasteners and said at least one cleaning pad is made from a material that is adherable to said at least one of hook and loop fasteners.

4. An apparatus as recited in claim 3, wherein said cleaning pad is coated with at least one of a sanitizing agent and a disinfectant.

5. An apparatus as recited in claim 4, including a supply of said cleaning pads.

6. An apparatus as recited in claim 5, wherein said supply of cleaning pads is provided in a reclosable container.

7. An apparatus as recited in claim 1, wherein said elongate member is made from a moldable plastic.

8. An apparatus as recited in claim 7, wherein said elongate member is made from polypropylene.

9. An apparatus as recited in claim 1, wherein the handle portion enables one handed operation of said apparatus.

10. An apparatus as recited in claim 1, wherein the overall length of said elongate member is at least 75 times the thickness of said intermediate portion and said cleaning pod of said elongate member.

11. An apparatus as recited in claim 1, wherein the width of said elongate member is at least 2 times the thickness of said intermediate portion and said cleaning pod of said elongate member.

12. An apparatus as recited in claim 1, wherein said intermediate portion of said elongate member has a length dimension which is at least 20 times a corresponding width dimension thereof.

13. An apparatus as recited in claim 1, wherein said elongate member has an overall length dimension that is as long as at least one of a full arm and a full leg medical cast.

14. An apparatus as recited in claim 1, wherein said apparatus is disposable.

15. An apparatus as recited in claim 1, wherein said cleaning pod includes a planar surface on which said at least one cleaning pad is releasably attached, said planar surface being recessed.

16. An apparatus for sanitizing the skin area of a cast wearer, said apparatus comprising:
    a thin, flexible and elongate member having a thickness that permits a portion of said member to be slid between the skin of a patient and the inner surface of a worn cast; and
    a cleaning pod formed on the distalmost end of said elongate member, said member including a handle portion that enables gripping of said apparatus at an opposite proximal end and an elongated intermediate section separating said handle portion and said cleaning pod, wherein a cleaning pad is secured on one side of said cleaning pod, said cleaning pod including means for releasably securing said cleaning pad thereto, said cleaning pad having a skin cleansing agent disposed thereon.

17. An apparatus as recited in claim 16, wherein said cleaning pod includes a planar surface having at least one of hook and loop fasteners, said cleaning pad being made from a material to permit adhesion thereby.

18. An apparatus as recited in claim 17, wherein said planar surface is recessed.

19. A method for periodically cleaning the skin area beneath the worn medical cast of an individual, said method comprising the steps of:
    securing a cleaning pad to the distalmost end of a thin elongate plastic member, said member having a thickness dimension permitting the distal end and a portion of an intermediate section of said elongate member to be inserted between the cast and the skin of the patient and a length dimension that permits the distal end of said member to be situated anywhere beneath the worn cast;
    gripping a handle portion at a proximal end of said member; and
    moving said flexible member solely using one hand gripping said handle portion so as to move said secured cleaning pad within the cast to clean the area of skin covered by the worn medical cast.

20. A method as recited in claim 19, including the additional steps of:
    removing said cleaning pad from the distal end of said flexible member when cleaning is completed; and
    replacing said cleaning pad.

* * * * *